Aug. 26, 1941. C. J. VAN BOURGONDIEN Plant Pat. 488
FREESIA PLANT
Filed April 29, 1941
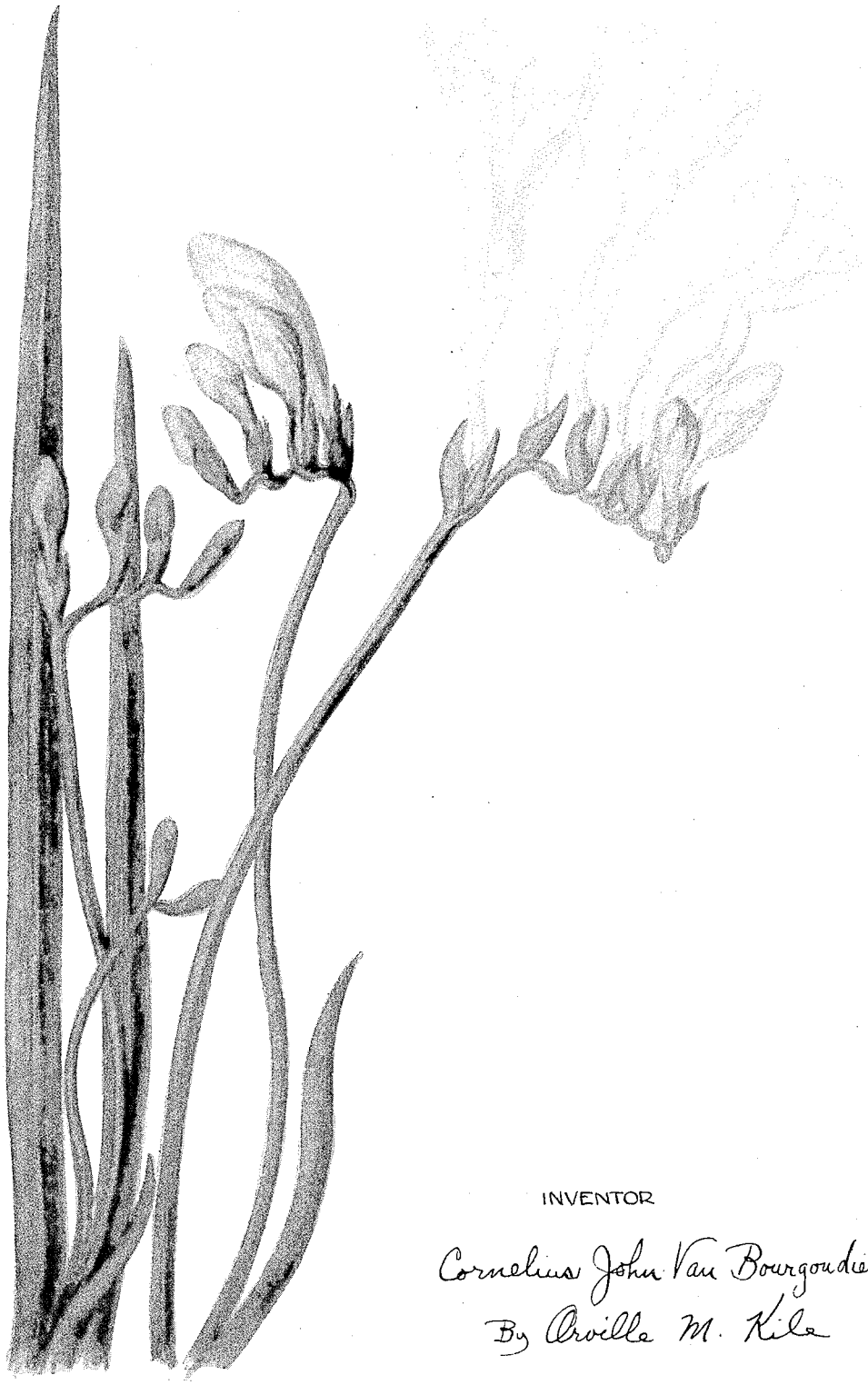
INVENTOR
Cornelius John Van Bourgondien
By Orville M. Kile
PLANT PATENT AGENT Patented Aug. 26, 1941

Plant Pat. 488

UNITED STATES PATENT OFFICE

488

FREESIA PLANT

Cornelius John Van Bourgondien, Babylon, N. Y., assignor to C. J. Van Bourgondien, Inc., Babylon, N. Y.

Application April 29, 1941, Serial No. 391,011

1 Claim. (Cl. 47—60)

My new invention relates to improvements in yellow freesia varieties, and falls in the class known as giant freesias. The principal object of my invention is to produce a sturdy freesia variety of yellow color, large size, and good keeping quality.

My new variety is a seedling and is the result of definite breeding efforts carried on by me. The seed parent was Albatre Supreme and the pollen parent Golden Daffodil. The new variety has been asexually reproduced for several years and its outstanding qualities have proved to be firmly fixed.

There is no other variety similar to this new variety but the known variety most like it in color is Golden Daffodil, one of its parents. However, this new variety is approximately twice the size of Golden Daffodil and therefore not in the same classification.

The foliage of this new variety is narrow but exceptionally abundant, there being approximately twice as much as on the ordinary freesia plant.

The flower stems are very tall and even the branched stems are long. Flower productivity is very prolific and the blooming season is long.

The original illustration accompanying this application shows a blooming spike with several branches containing buds, together with some of the foliage. All are shown in approximately natural colors and very slightly enlarged.

Following is a detailed description of the plant and flower of this new freesia variety. Where color plate numbers are given they refer to Ridgway's Color Standards and Nomenclature.

*The plant*

Growth habits: This plant belongs to the class known as giant freesias and grows to a height of 36 inches. The growth is very strong and sturdy and production of corms and flowers is very prolific.

Blooming season: Approximately six weeks' duration.

Corms: Very large both in size and number, a single plant frequently producing 15 or 16 corms.

Stems: Very sturdy, tall and upright; well-branched and long, main flower stems averaging 22 to 24 inches in length. Secondary stems are also of good length and frequently branched. Main stems hold their flowers well above the foliage but some of the branched heads mingle with the foliage. Color is approximately Parrot Green (Plate VI).

Foliage: Abundant; very tall and narrow, greatest width about ½ inch, average height 24 inches; points long and slender; midrib prominent; slightly darker than stems, between Parrot Green (Plate VI) and Spinach Green (Plate V).

*The flower*

Arrangement: The flowers of a single stem or spike are borne upright along a jointed rachis which is slightly irregular and usually extends approximately at right angles to the stem, allowing the first blossom of the series to appear to be a vertical extension of the stem or peduncle. The usual spike contains five of these blossoms, three of which may be open at the same time.

Sepals: Two; enclosing ovary; unusually long and pointed; approximately Parrot Green (Plate VI).

Form: Perianth long and funnel shaped, with tube or throat gradually tapering. Petals divided deeply, distinct without overlapping. Sometimes one or two of the petals spread at right angles, but in general the great length of the perianth is emphasized by the continuous line of the petals in funnel shape.

Size: Very long, averaging 3 to 3½ inches. Width if petals are spread, 2½ to 2¾ inches. However the flowers ordinarily do not spread at right angles and do not appear to have such great width.

Fragrance: Pronounced and pleasing.

Petals: Six; long; lobes separate, with little or no overlapping; gently rounded at top but a slight reflexing of some of the petals gives the effect of pointed tips.

Color: Mature flower is approximately Primuline Yellow (Plate XVI) at the base; opening flower has slightly greenish tint. The Primuline Yellow is uniformly distributed upward to the point where the perianth separates into lobes or petals. From that point a stripe of much lighter color extends up the center of each petal to its tip. The color of this stripe ranges from creamy white to Naples Yellow (Plate XVI), and is not visible on the inner surface of the petals. At least one of the petals or lobes is Light Cadmium (Plate IV) to Cadmium Yellow (Plate V) on most of its inner surface and this same bright yellow to orange color edges its outer surface.

Keeping quality: Good.

Reproductive organs:

*Stamens.*—Three. Attached to the perianth upward to the top of the throat, from which point they are free and extend about one inch. Filaments are yellow and are topped with pure white anthers.

*Pistils.*—Compound, with six branches; white; situated among the stamens and arising only slightly above them; free its entire length from ovary to its tip.

Having thus disclosed my invention, I claim:

The new and distinct variety of giant freesia plant herein shown and described, characterized particularly by its vigorous, upright growth; its abundant, tall, narrow foliage; its prolific production of large corms; its long blooming season; its strong, tall, upright flower stems which are well branched; and its fragrant, large, exceptionally long flowers of good keeping quality and of yellow shades as indicated.

CORNELIUS J. VAN BOURGONDIEN.